United States Patent [19]

Languet et al.

[11] Patent Number: 5,747,063
[45] Date of Patent: May 5, 1998

[54] THERAPEUTIC ELEMENTS FOR THE ORAL ADMINISTRATION OF MEDICATION TO ANIMALS AND PROCESS FOR MAKING SAME

[75] Inventors: Bernard Languet, Les Cotes D'Arey; Philippe Desmettre, Ecully, both of France

[73] Assignee: Rhone Merieux, Lyon, France

[21] Appl. No.: 896,905

[22] Filed: Jun. 11, 1992

Related U.S. Application Data

[63] Continuation of Ser. No. 592,018, Oct. 2, 1990, abandoned.

[30] Foreign Application Priority Data

Oct. 2, 1989 [FR] France ............... 89 12831

[51] Int. Cl.$^6$ ................................................ A23K 1/165
[52] U.S. Cl. ...................... 424/442; 424/439; 426/1
[58] Field of Search .................. 424/442, 439; 426/1

[56] References Cited

U.S. PATENT DOCUMENTS

| | | | |
|---|---|---|---|
| 3,607,295 | 9/1971 | Morgan | 99/3 |
| 3,829,564 | 8/1974 | Merry | 424/78 |
| 4,666,717 | 5/1987 | Smith | 426/1 |
| 4,861,586 | 8/1989 | Schneider | 424/442 |

FOREIGN PATENT DOCUMENTS

| | | |
|---|---|---|
| A-240826 | 3/1987 | European Pat. Off. . |
| 2144599 | 2/1973 | France . |
| WO 89/12393 | 12/1989 | WIPO . |

*Primary Examiner*—D. Gabrielle Phelan
*Attorney, Agent, or Firm*—Larson & Taylor

[57] ABSTRACT

The therapeutic elements for oral administration of medication to animals comprise an active principle contained in a craved for envelope. The envelope (1) comprises, in admixture, one or more craved for materials and one or more substances agglomerating the craved for materials, the envelope possessing a high mechanical and thermal resistance, and being previously formed into a hollow shape appropriate for consumption by the animal, and defining an internal volume, such internal volume being filled by a craved for binder (3) and comprising the active principle (2), the binder closely conforming the internal shape of the envelope (1) in order to provide a continuity between the envelope (1) and the active principle (2).

14 Claims, 1 Drawing Sheet

THERAPEUTIC ELEMENTS FOR THE ORAL ADMINISTRATION OF MEDICATION TO ANIMALS AND PROCESS FOR MAKING SAME

This application is a continuation of application Ser. No. 07/592,018 filed Oct. 2, 1990, now abandoned.

This invention relates to therapeutic elements for oral administration of medication such as a vaccine, a medicinal substance or the like to wild or domestic animals.

This invention also relates to a process for making these therapeutic elements.

The intake of medication by domestic animals is most oftenly effected through parenteral administration after having contained the animal.

When these animals are raised on a larger scale, it is difficult and sometimes dangerous to contain them for the administration of vaccines or medication.

For wild animals, the capture of a few individuals, which comprises similar risks and difficulties, may be considered but it seems unrealistic to foresee the treatment of all the members of a same species found in a given territory.

It was contemplated to produce elements containing effective medications and sufficiently craved for to be suitable for oral administration and for distribution in extensive areas in order to treat large numbers of wild animals, but also with the view to eventually treat individuals which belong to domestic animal species that are not desirable or possible to capture.

According to European patent application EP-A-240 826, there is disclosed in the prior art a process for the preparation of a bait, in which a support substance is cast. The support substance comprises a lipid component, a component used to stabilize the shape of the bait and an attractive substance for which animals crave. To prepare this bait, the support substance is first cast at the bottom of a mold. The active substance is then deposited on the layer formed by the support substance and the support substance is again cast in the mold in such a manner as to trap the active substance in a coating of support substance.

This type of process presents a certain number of drawbacks. The casting requires the use of substances having a relatively good fluidity at the desired casting temperatures. Furthermore, if one wishes to have a casting temperature compatible with the preservation of the active principle, it is necessary to use substances whose low melting point will be in the vicinity of the highest temperatures at which the system will be used, bearing in mind the resulting inconveniences with regard to the overall stability of the bait. Hence, the two-step casting of the support substance may lead to a non-neglectable fragility in the area of the joint formed by the two separate castings. This, combined with the low mechanical resistance of the support substance, may render the bait unsuitable for presently existing wide scale distribution techniques such as aerial release.

One object of the present invention is therefore to provide therapeutic elements for oral administration of medication to animals that are attractive to the animal, for which the targeted animal will crave and which exhibit high mechanical and thermal resistance, thereby permitting distribution through aerial release in all climatic conditions found in the distribution zone.

Another object of the present invention is to provide therapeutic elements whose structure, texture and dimensions enable an effective intake of medication by the animal.

Another object of the invention is to provide therapeutic elements which are inexpensive and easy to prepare.

Another object of the present invention is to prepare therapeutic elements having an enhanced resistance to alteration in their distribution medium on an extensive period of time.

The present invention also relates to a process for the preparation of these therapeutic elements.

Another object of the present invention is to provide such a process which can be applied even to heat sensitive medication.

Another object of the present invention is to provide a process which is relatively easy to carry out, relatively inexpensive and easily automated.

The invention relates to a therapeutic element for oral administration of medication to animals, which comprises an active principle contained in a craved for envelope, characterized in that the envelope comprises, in admixture, one or more craved for materials and one or more substances agglomerating the craved for materials, the envelope possessing a high mechanical and thermal resistance, and being previously formed into a hollow shape, open at each each end, appropriate for consumption by the animal, and defining an internal volume, such internal volume being filled by a craved for binder and comprising the active principle, the binder closely conforming to the internal shape of the envelope in order to provide a continuity between the envelope and the active principle.

Preferably, the envelope has a tubular shape, more preferably a parallelepiped shape.

Advantageously, the envelope may be rendered hydrophobic through the use of hydrophobic agglomerating substances or by incorporating a hydrophobic additive such as an oil, etc.

The craved for binding material may be similar to the envelope. It preferably possesses one, many or all the following properties:

it is heat resistant;

it participates, in close relationship with the envelope, to the elasticity or the plasticity of the element in order to increase its resistance to shock;

it is hydrophobic;

it appears at the surface, especially when the envelope has a tubular shape.

The medication may be contained in a container such as a pouch, a capsule, etc. or it may be in the form of a tablet or the like.

The medication may also be disseminated in the binding material or admixed to it.

The medication may be in liquid or solid form.

The agglomerating material may be preferably selected from, polyosides, starches, cellulose, vegetable or animal waxes, silicones, synthetic polymers, preferably hydrophobic, long chain fatty acids, preferably those having 20 carbon atoms or more, etc.

The agglomerating material may preferably be a polymer of the type used in the preparation of food for shrimps and fish such as those described in U.S. Pat. Nos. 4,576,821, 4,666,717 and 4,741,904. Ethylene-vinyl acetates represent a suitable example.

The envelope of the present invention may preferably have one of the compositions described in the above-mentioned U.S. Patents or the composition of the shrimp food sold under the trade mark CRAWDEAUX by DU PONT DE NEMOURS.

For foxes and dogs, the baits may have preferably about 50 mm in length, 32 mm in width, 20 mm in height and the cavity of the tubular envelope may have about 50 mm in length, 23 mm in width and 9 mm in height.

In accordance with a preferred embodiment of the invention, the bait may comprise a con-toxic marker, for example an antibiotic such as tetracycline chlorydrate. The latter may particularly be contained in the envelope in a preferred amount of 150 mg for each bait.

The present invention also relates to a process for preparing these therapeutic elements, characterized in that there is shaped an envelope comprising, in admixture, one or more craved for materials and one or more substances agglomerating the craved for material and having a high thermal and mechanical resistance whereby the shaping confers to the envelope a hollow form defining an internal volume and characterized in that the active principle and a craved for binding material are placed in the internal volume in such a manner as to ensure that the binding material closely conforms to the internal shape of the envelope.

Preferably, the envelope will have a tubular shape such as a parallelepiped shape. This envelope may also have any other appropriate shape such as a cylindrical shape.

Preferably, the envelope is obtained through an extrusion process.

In a first preferred embodiment of the present invention, the active principle is placed in the internal volume of the envelope and the binding material is then cast in the internal volume of the envelope.

In a second preferred embodiment of the invention, the binding material containing the active principle is cast in the internal volume of the envelope.

The process of the present invention may easily be applied on an industrial scale.

The elements prepared according to the process may be stored at room temperature or at low temperature in accordance with the storage requirements of the active principle.

BRIEF DESCRIPTION OF THE DRAWINGS

The invention will now be described in more details through an example of the process of the present invention, illustrated by the annexed drawings in which.

Figure 1:
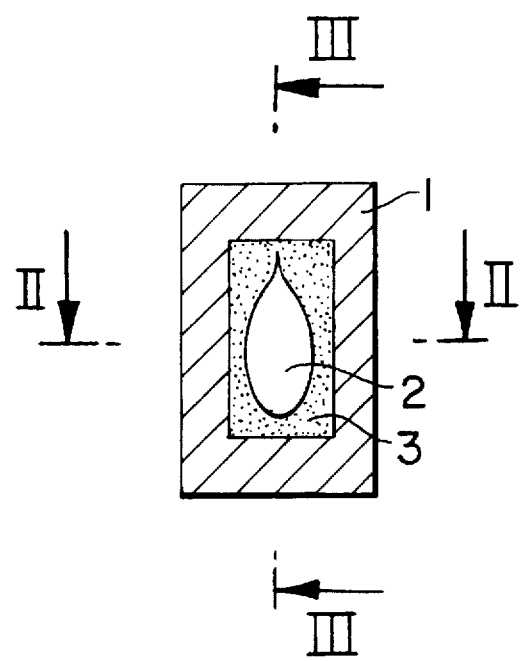
FIG. 1 represents a transversal cross-section of an element produced in accordance with the process of the present invention.
Figure 2:
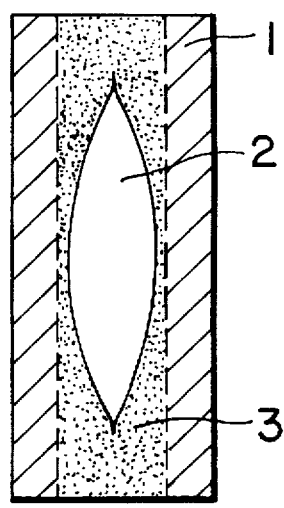
FIG. 2 represents a longitudinal cross-section along line II—II of FIG. 1.
Figure 3:
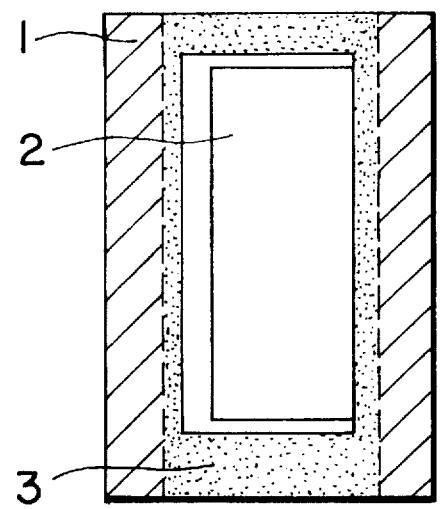
FIG. 3 represents a longitudinal cross-section along line III—III of FIG. 1.

The tubular envelope 1 has first been produced through an extrusion process at a temperature of about 100° C. The extruded mixture is initially constituted by fish oil, fish food and ethylene-vinyl acetate in the preferred proportions set forth in the above-noted U.S. Patents.

The dimensions of the envelope 1 are chosen as a function of the animals to whom the therapeutic elements are to be administered.

Once the envelope 1 has been cooled (the envelope is relatively rigid and is hydrophobic) and set at the desired length, a pouch 2 made of plastic material (thermally bounded polyethylene) and containing the active principle (for example an anti-rabies vaccine) in a volume of 2.5 ml is placed in the envelope cavity.

Thereafter, there is cast in the cavity a binding substance 3 consisting of a mixture of fatty components having a low melting point, remaining pasty at high temperatures and exhibiting no brittleness at low temperatures.

This mixture of fatty components comprises, among other substances, a substance which is attractive to the animal and for which the targeted animal will crave.

Physical and storage properties

Behaviour tests at temperatures ranging between −20° C. and 45° C. have demonstrated that the structure of the element obtained through the process referred to above was well-maintained within this temperature range. At the highest temperature, the binder has a pasty consistence that does not hinder efficiency because of the behaviour of the envelope.

These experiments have also shown that the products had a very good shock resistance when released from a helicopter at a height higher than 100 m on a concrete surface. None of the elements was deteriorated.

Some experiments were also conducted to evaluate the efficiency of the element of the present invention on foxes and dogs. The results obtained have demonstrated the efficiency of the bait towards the animals and the structure of the bait was found to be particularly appropriate for an efficient intake of the active principle (suitable delivery of the liquid active principle in the oral cavity).

Attracting properties

A first experiment was conducted on 10 dogs placed in individual box stalls. Each dog received an element according to the present invention (produced through the above-noted process) mixed to its daily food intake.

24 hours following distribution, 100% of the elements had been consumed and the coloured marker used allowed to conclude that the contents of the pouch had been spread out in the mouth of 9 dogs out of 10.

A second experiment was conducted using similar conditions on 18 dogs and has led to similar results.

Furthermore, all the dogs that received in the following days one or two of the elements according to the present invention consumed these elements within 24 hours.

Efficiency

Efficiency was evaluated through an oral anti-rabies vaccination of carnivorouses. The vaccine used was a vaccine/ glycoprotein G recombinant whose activity had previously been demonstrated.

18 red foxes were divided in 3 groups (A, B, C) of 6 individuals each and each animal was placed in an individual cage.

Group A received 1 element on day 0 (D0).

Group B received 2 elements (on D0 and on D1).

Group C received 3 elements (D0, D1 and D2).

4 foxes were used as controls.

For each fox, the level of anti-rabies antibodies was monitored.

After a period of 20 days following vaccination, the foxes were tested intra-muscularly (strong dose of rabies virus).

All the non-vaccinated controls died.

Results are shown in the following table:

|  | Seroconversion rate | Protection rate |
| --- | --- | --- |
| Group A | 4 | 5 |
| Group B | 5 | 6 |
| Group C | 5 | 5 |

A similar experiment was conducted on 18 dogs that had never received an anti-rabies vaccine. Group A received 1 element at D0, Group B received 2 elements at D0 and D3 and Group C received 3 elements at D0, D3 and D4.

The seroconversion rates were as follows:

Group A=5,

Group B=6,

Group C=6.

The process of the present invention may be used in the preparation of elements to be used for wild or domestic animals. Among such animals, there may be mentioned, foxes, skunks, raccoons, jackals, stray dogs, civets, mongooses, wild cats (for the administration of anti-rabies vaccines for example) as well as domestic species such as bovines, ovines, caprines, equines, porcines, dogs and cats, etc.

Obviously, the active principle can also be in solid, powder or paste form. It can be a vaccine, an antibiotic, a hormone, an antiparasitic, etc.

The present invention is not limited to the embodiment described and represented but comprises any variant falling within the knowledge or persons skilled in the art.

We claim:

1. A therapeutic element for oral administration of targeted animals comprising
    a preformed extruded hollow shaped envelope open at each end, defining an internal volume and of a size consumable by said animals, said hollow shaped envelope being comprised of at least one edible substance attractive to the targeted animals in admixture with at least one material agglomerating said substances; and
    an edible binding material attractive to the targeted animals containing an oral medication, said binding material filling said internal volume and closely conforming to the internal shape of hollow-shaped envelope so as to provide a continuity between said envelope and said medication and thus provide a substantially shock-resistant element.

2. Therapeutic elements according to claim 1, wherein said envelope has a tubular shape.

3. Therapeutic elements according to claim 1, wherein said envelope has a parallelepiped shape.

4. Therapeutic elements according to claim 1, wherein said envelope is hydrophobic.

5. Therapeutic elements according to claim 4, wherein the agglomerating substances confer a hydrophobic character to said envelope.

6. Therapeutic elements according to claim 4, wherein said envelope further comprises an additive conferring a hydrophobic character to said envelope.

7. Therapeutic elements according to claim 1, wherein said craved for binding material has the composition of said envelope.

8. Therapeutic elements according to claim 1, wherein said binding material is heat resistant.

9. Therapeutic elements according to claim 1, wherein said envelope and said binding material are elastic.

10. Therapeutic elements according to claim 1, wherein said envelope and said binding material are plastic.

11. Therapeutic elements according to claim 1, wherein said binding material is hydrophobic.

12. Therapeutic elements according to claim 2, wherein said binding material is apparent at the surface of said element.

13. Therapeutic elements according to claim 1, wherein said medication is contained in a container.

14. Therapeutic elements according to claim 1, wherein said medication is disseminated or admixed in the binding material.

* * * * *